(12) United States Patent
Hegel et al.

(10) Patent No.: US 8,597,943 B2
(45) Date of Patent: Dec. 3, 2013

(54) METHOD FOR IMPROVED SINGLE CELL CLONING

(75) Inventors: Kolja Hegel, Warthausen (DE); Olaf Kruger, Ulm (DE); Aziz Cayli, Ulm (DE)

(73) Assignee: CELLCA GmbH (DE)

( * ) Notice: Subject to any disclaimer, the term of this patent is extended or adjusted under 35 U.S.C. 154(b) by 0 days.

(21) Appl. No.: 13/263,404

(22) PCT Filed: Apr. 9, 2010

(86) PCT No.: PCT/EP2010/002217
§ 371 (c)(1),
(2), (4) Date: Oct. 7, 2011

(87) PCT Pub. No.: WO2010/115634
PCT Pub. Date: Oct. 14, 2010

(65) Prior Publication Data
US 2012/0021510 A1    Jan. 26, 2012

(30) Foreign Application Priority Data
Apr. 9, 2009  (EP) .................................... 09005211

(51) Int. Cl.
*C12N 5/00* (2006.01)
*C12N 5/02* (2006.01)

(52) U.S. Cl.
USPC ........... 435/325; 435/383; 435/388; 435/389; 435/407

(58) Field of Classification Search
USPC ......................................... 435/388, 389, 407
See application file for complete search history.

(56) References Cited

FOREIGN PATENT DOCUMENTS

| WO | WO 2006/047380 A2 | 5/2006 |
|---|---|---|
| WO | WO 2008/009641 A1 | 1/2008 |
| WO | WO 2009/030720 A2 | 3/2009 |

OTHER PUBLICATIONS

Keenan et al. "The role of recombinant proteins in the development of serum-free media", Cytotechnology 50: 49-56, 2006.*
Mattanovich et al. "Applications of cell sorting in biotechnology", Microbial Cell Factories 5: 1-12, 2006.*
GIBCO® "A guide to serum-free cell culture", copyright 2003, available online 2008.*
Keenan, J., et al., "The role of recombinant proteins in the development of serum-free media," *Cytotechnology*, vol. 50(1-3), pp. 49-56 (Mar. 2006).
Kuchenbecker, M., et al., "Establishment of Recombinant CHO Cell Lines Under Serum-free Conditions," *Cell Technology for Cell Products*, pp. 57-61 (Jun. 1, 2007, Proceedings of the 19th ESACT Meeting, Harrogate, UK, Jun. 5-8, 2005).
Yamamoto, T., et al., "Stimulation of cAMP signaling allows isolation of clonal pancreatic precursor cells from adult mouse pancreas," *Diabetologia*, vol. 49(10), pp. 2359-2367 (Oct. 2006).
Yamauchi, T., et al., "Production of Human Antithrombin-III in a Serum-free Culture of CHO Cells," *Bioscience, Biotechnology and Biochemistry*, vol. 56(4), pp. 600-604 (Apr. 1992).

* cited by examiner

*Primary Examiner* — Ruth Davis
*Assistant Examiner* — Emily Cordas
(74) *Attorney, Agent, or Firm* — Kilpatrick Townsend & Stockton LLP

(57) ABSTRACT

The present invention relates to methods for the cultivation of a population of cells in a serum free cell culture medium, wherein the population of cells has a cell concentration of less than 100 cells/ml, wherein a serum free cell culture medium containing recombinant albumin and recombinant transferrin is used.

17 Claims, 5 Drawing Sheets

METHOD FOR IMPROVED SINGLE CELL CLONING

CROSS-REFERENCES TO RELATED APPLICATIONS

Figure 1:
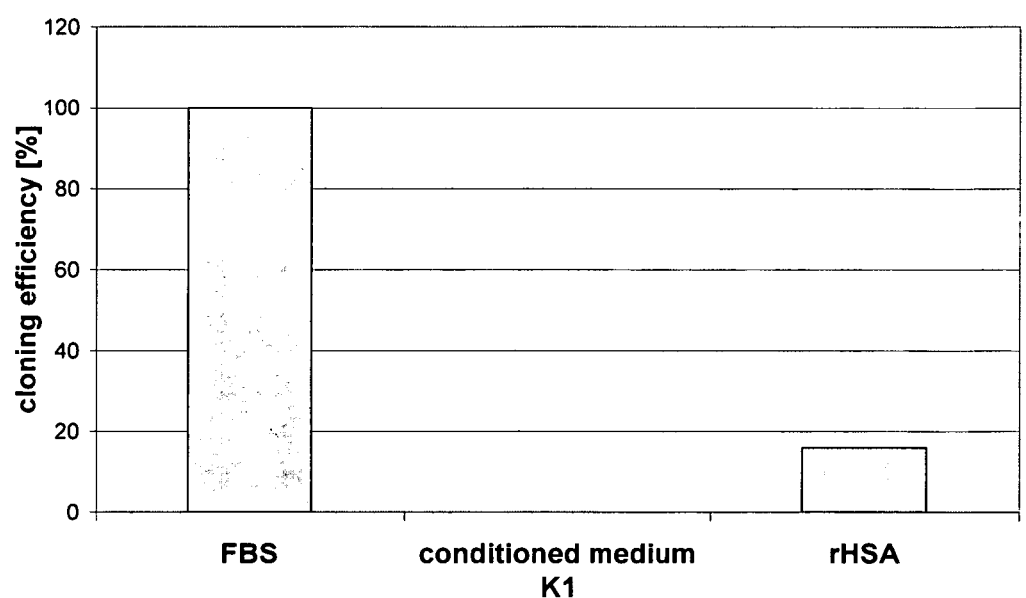

The present application is a U.S. National Phase of PCT/EP2010/002217, filed Apr. 9, 2010, which claims the benefit of European Application No. 09005211.9, filed on Apr. 9, 2009, the disclosures of which are hereby incorporated herein by reference in their entirety.

The present invention relates to methods for the cultivation of a population of cells in a serum free cell culture medium, wherein the population of cells has a cell concentration of less than 100 cells/ml, wherein a serum free cell culture medium containing recombinant albumin and recombinant transferrin is used. The present invention also relates to the use of a serum free cell culture medium containing recombinant albumin and recombinant transferrin for the cultivation of a population of cells with a cell concentration of less than 100 cells/ml. The present invention relates also to a cell population with a cell concentration of less than 100 cells/ml cultivated in a serum free cell culture medium containing recombinant albumin and recombinant transferrin. Typical cell culture media are often supplemented with undefined additives, like fetal bovine serum (FBS). Such additives provide carriers for labile or water insoluble components, provide growth factors, and protect cells from physical stress. The use of serum has on the other hand several drawbacks. Serum is an uncharacterised mixture of substances which may vary from lot to lot. However, the main disadvantage of serum or other supplements from animal or human origin is the risk of contamination with adventitious agents, e.g. mycoplasma, prions and viruses.

To overcome the pathogenic contamination risk associated with serum, serum free media have been developed in the past. Serum free media are often supplemented with serum substitutes, such as growth factors, cytokines, albumin, insulin and transferrin. These proteins are generally isolated from an animal source, so that the potential risk of contamination of media with pathogens still exists. For example, cell culture could be facilitated using bovine serum albumin (BSA), human serum albumin (HSA) or transferrin isolated from an animal or human source (U.S. Pat. No. 6,733,746). This approach still runs the risk of introducing adventitious pathogens into the cell culture, such as HIV, Creutzfeld Jakob agent or hepatitis viruses from HSA. The pathogens impact negatively the application of culture media in the production of animal and human therapeutics. Culture media have been described which only contain recombinantly produced proteins and thus reduce the risk of pathogenic contaminations. There are published media containing recombinant albumin together with additional animal drived components (WO2008009642) and culture media containing recombinant albumin and recombinant insulin (US20060115901).

A common supplement that is routinely added to serum free media is transferrin. Transferrin is usually isolated from animal or human sources and is added into the serum free culture media to supply cells with iron. Mechanisms of iron uptake by mammalian cells have been reviewed by Qian, Z. M. and Tang, P. L., 1995, Biochim. Biophys. Acta, 1269: 205-214. Further publications exist indicating that transferrin might be a growth factor supporting cell proliferation. On the other hand it has been shown that transferrin-receptor deficient cells can proliferate at rates comparable to wild type cell, indicating that this receptor does not belong to the family of growth factor receptors (Chan, R. et. al., 1992, Experimental cell research 202: 326-336). In case of transferrin-receptor deficiency, cells can take up iron through a non-specific receptor-independent mechanism. Generally, there are three mechanisms by which cells can take up iron: 1. from transferrin through a receptor-dependent pathway, 2. from transferrin through a receptor-independent pathway (non-specific), 3. from inorganic iron salts, e.g. $FeSO_4$ (Chan, R. et. al., 1992, Experimental cell research 202: 326-336). The later way of iron uptake is the background of many inorganic iron chelates added into the culture media, supplying cells with iron and neglecting the other effects of transferrin (EP1210410). Due to the non-specific iron uptake of cells from inorganic iron salts, many cell culture media have been developed completely free of any proteins. Interestingly, cells grow in protein free media very well, so that today state of the art culture media are free of any proteins. In summary, the published data demonstrates that transferrin is able to mediate iron uptake in mammalian cells. However, because cells can take up iron also from inorganic iron chelates, transferrin is not necessarily required for iron supplement. Up to date, it is not clear if transferrin, besides its assignment as iron provider, has further growth-factor-like effects on cells.

During production of therapeutic proteins with animal cell cultures, it is important to demonstrate the clonality of the production cell line. This means, that genetically modified production cell lines should originate from a single precursor cell which has been single cell cloned by seeding only one cell per well in a culture dish. Cells in single cell status are exposed to rapidly changing environmental conditions, like pH changes, temperature changes, or deleterious effects of accumulated oxidative media products. In contrast, a cell co-cultured in a cell population receives proliferation and survival supporting components like cytokines from its neighbouring cells. When this support is omitted during single cell cultivation, many clones cannot survive the elevated culture stress. When a single clone is seeded into a culture dish, like a 96-well plate, the clone does not receive stimulating support from neighbours. This often results in cell death or non-proliferative behaviour. To circumvent these difficulties, it is common that single cell cloning is performed in the presence of fetal bovine serum (FBS) in the culture medium. Hence, it is of great interest to develop a serum free single cell cloning medium, due to above mentioned disadvantages of serum.

A method has been developed for culturing CHO cells at very low cell densities in a serum free medium. Among others, the medium contains recombinant albumin and recombinant insulin (US20060115901). It is common that conditioned media are added in serum free single cell cloning media. Conditioned media contain cytokines produced by the same cell population and therefore should promote the clonal growth of a single cell (WO2005014799). However, the concentration of the cytokines in conditioned media is low and conditioned media contain also growth inhibiting cellular toxic metabolites so that the growth promoting effects of such media are limited.

Another method is the co-culturing of the actual production clone with parental cells. The so-called feeder cells can be radiated in order to deprive the cells of the ability to grow. The non-growing feeder cells would release growth factors stimulating the production clone for division (EP1176194, US2005/0059146). The drawback of cultures utilizing feeder cells is the difficulty to separate the production clone from the feeder cells. It has to be demonstrated that the feeder cells are not attached to the production clone.

In summary, published data demonstrates that there is a need for new and simple methods for single cell cloning of cells in serum free media.

The technical problem underlying the present invention is to provide methods and cell culture media to overcome the disadvantages of the state of the art.

A further technical problem underlying the present invention is to provide a more simple method for single cell cloning of cells, especially in serum free media.

A further technical problem underlying the present invention is to provide a more simple method for the cultivation of populations of cells with low cell concentration in media, especially in serum free media.

The present invention solves the above-identified problem by the provision of the teaching of the independent claims.

In particular, the present invention provides a method for the cultivation of a population of cells in a serum free cell culture medium, wherein the population of cells has a cell concentration of less than 100 cells/ml, comprising the steps a) culturing a population of cells at a cell concentration greater than about 100 cells/ml, especially greater than 100 cells/ml, in a first serum free cell culture medium, b) reducing the cell concentration to less than about 100 cells/ml, especially to less than 100 cells/ml, and c) culturing the cells in a second serum free cell culture medium, wherein the second serum free cell culture medium contains recombinant albumin and recombinant transferrin.

In particular, the present invention provides a method for the cultivation of a population of cells in a serum free cell culture medium, wherein the population of cells has a cell concentration of less than 100 cells/ml, comprising the steps a) culturing a population of cells at a cell concentration greater than about 100 cells/ml, especially greater than 100 cells/ml, in a first serum free cell culture medium, b) reducing the cell concentration to less than about 100 cells/ml, especially to less than 100 cells/ml, and c) contacting the cells with a second serum free cell culture medium, wherein the second serum free cell culture medium contains recombinant albumin and recombinant transferrin.

In a preferred embodiment of the invention the cell concentration in step a) is greater than 200 cells. In a preferred embodiment of the invention the cell concentration in step a) is greater than about 200 cells. In a preferred embodiment of the invention the cell concentration in step a) is greater than 500 cells. In a preferred embodiment of the invention the cell concentration in step a) is greater than about 1000 cells. In a preferred embodiment of the invention the cell concentration in step a) is greater than 1000 cells. In a preferred embodiment of the invention the cell concentration is reduced in step b) to less than 50 cells/ml. In a preferred embodiment of the invention the cell concentration is reduced in step b) to less than 10 cells/ml. In a preferred embodiment of the invention the cell concentration is reduced in step b) to 1 cell/ml.

In a preferred embodiment of the invention the cell population is reduced in step b) to 1 cell. Accordingly, in a preferred embodiment of the invention the cell population contains at the beginning of step c) 1 cell.

In a preferred embodiment of the invention the cell population is reduced in step b) to 1 cell per culture dish. Accordingly, in a preferred embodiment of the invention the cell population contains at the beginning of step c) 1 cell per culture dish.

In a preferred embodiment of the invention the cell population is reduced in step b) to 1 cell per culture well. Accordingly, in a preferred embodiment of the invention the cell population contains at the beginning of step c) 1 cell per culture well. A person skilled in the art knows several culture dishes and culture wells which are suitable to culture cells, especially to culture a cell population. A person skilled in the art knows also several culture dishes and culture wells which are suitable to culture a cell population having a cell concentration of less than 100 cells/ml. A person skilled in the art knows also several culture dishes and culture wells which are suitable to culture a cell population having a cell concentration of less than 100 cells in total, especially a cell population consisting of only one single cell.

Furthermore, the present invention provides a method for the cultivation of a single cell in a serum free cell culture medium, comprising the steps a) culturing a population of cells at a cell concentration greater than about 100 cells/ml, especially greater than 100 cells/ml, in a first serum free cell culture medium, b) isolating a single cell out of the population of cells, and c) culturing the single cell in a second serum free cell culture medium, wherein the second cell culture medium contains recombinant albumin and recombinant transferrin.

Furthermore, the present invention provides a method for the cultivation of a single cell in a serum free cell culture medium, comprising the steps a) culturing a population of cells at a cell concentration greater than about $10^3$ cells/ml, especially greater than $10^3$ cells/ml, in a first serum free cell culture medium, b) isolating a single cell out of the population of cells, and c) contacting the single cell with a second serum free cell culture medium, wherein the second cell culture medium contains recombinant albumin and recombinant transferrin.

In a preferred embodiment of the invention the cell concentration in step a) is greater than 100 cells. In a preferred embodiment of the invention the cell concentration in step a) is greater than about 200 cells. In a preferred embodiment of the invention the cell concentration in step a) is greater than 500 cells. In a preferred embodiment of the invention the cell concentration in step a) is greater than about 1000 cells. In a preferred embodiment of the invention the cell concentration in step a) is greater than 10000 cells. In a preferred embodiment of the invention the cell concentration in step a) is greater than about 100000 cells. In a preferred embodiment of the invention the cell concentration in step a) is greater than 1000000 cells.

In a preferred embodiment of the invention the cell concentration in step a) is greater than 100 cells/ml. In a preferred embodiment of the invention the cell concentration in step a) is greater than about 200 cells/ml. In a preferred embodiment of the invention the cell concentration in step a) is greater than 500 cells/ml. In a preferred embodiment of the invention the cell concentration in step a) is greater than about 1000 cells/ml. In a preferred embodiment of the invention the cell concentration in step a) is greater than 10000 cells/ml. In a preferred embodiment of the invention the cell concentration in step a) is greater than about 100000 cells/ml. In a preferred embodiment of the invention the cell concentration in step a) is greater than 1000000 cells/ml.

In a preferred embodiment of the invention the cells of the population of cells do not require recombinant transferrin and/or recombinant albumin for growth, when the cells are cultured at a cell concentration greater than about 100 cells/ml. In a preferred embodiment of the invention the cells of the population of cells do not require recombinant transferrin and/or recombinant albumin for growth, when the cells are cultured at a cell concentration greater than 100 cells/ml. In a preferred embodiment of the invention the cells of the population of cells do not require recombinant transferrin and/or recombinant albumin for growth, when the cells are cultured at a cell concentration greater than about 200 cells/ml. In a preferred embodiment of the invention the cells of the population of cells do not require recombinant transferrin and/or recombinant albumin for growth, when the cells are cultured at a cell concentration greater than 200 cells/ml. In a preferred embodiment of the invention the cells of the population of cells do not require recombinant transferrin and/or recombinant albumin for growth, when the cells are cultured at a cell concentration greater than about 500 cells/ml. In a preferred embodiment of the invention the cells of the population of cells do not require recombinant transferrin and/or recombinant albumin for growth, when the cells are cultured at a cell concentration greater than 500 cells/ml. In a preferred embodiment of the invention the cells of the population of cells do not require recombinant transferrin and/or recombinant albumin for growth, when the cells are cultured at a cell concentration greater than about $10^3$ cells/ml. In a preferred embodiment of the invention the cells of the population of cells do not require recombinant transferrin and/or recombinant albumin for growth, when the cells are cultured at a cell concentration greater than $10^3$ cells/ml. In a preferred embodiment of the invention the cells of the population of cells do not require recombinant transferrin and/or recombinant albumin for growth, when the cells are cultured at a cell concentration greater than about $10^4$ cells/ml. In a preferred embodiment of the invention the cells of the population of cells do not require recombinant transferrin and/or recombinant albumin for growth, when the cells are cultured at a cell concentration greater than $10^5$ cells/ml. In a preferred embodiment of the invention the cells of the population of cells do not require recombinant transferrin and/or recombinant albumin for growth, when the cells are cultured at a cell concentration greater than about $10^6$ cells/ml.

In a preferred embodiment of the invention the cells of the population of cells do not require recombinant transferrin for growth, when the cells are cultured at a cell concentration greater than about 100 cells/ml. In a preferred embodiment of the invention the cells of the population of cells do not require recombinant albumin for growth, when the cells are cultured at a cell concentration greater than about 100 cells/ml. In a preferred embodiment of the invention the cells of the population of cells do not require recombinant transferrin for growth, when the cells are cultured at a cell concentration greater than 100 cells/ml. In a preferred embodiment of the invention the cells of the population of cells do not require recombinant albumin for growth, when the cells are cultured at a cell concentration greater than 100 cells/ml. In a preferred embodiment of the invention the cells of the population of cells do not require recombinant transferrin for growth, when the cells are cultured at a cell concentration greater than about 1000 cells/ml. In a preferred embodiment of the invention the cells of the population of cells do not require recombinant albumin for growth, when the cells are cultured at a cell concentration greater than about 1000 cells/ml. In a preferred embodiment of the invention the cells of the population of cells do not require recombinant transferrin for growth, when the cells are cultured at a cell concentration greater than 1000 cells/ml. In a preferred embodiment of the invention the cells of the population of cells do not require recombinant albumin for growth, when the cells are cultured at a cell concentration greater than 1000 cells/ml.

In a preferred embodiment of the invention the cells of the population of cells are cells which are able to grow in serum free medium. a preferred embodiment of the invention the cells of the population of cells are cells which are adapted to grow in an serum free medium.

In a preferred embodiment of the invention the cells of the population of cells are cells which are able to grow in animal component free medium. In a preferred embodiment of the invention the cells of the population of cells are cells which are adapted to grow in an animal component free medium. In a preferred embodiment of the invention the cells of the population of cells are cells which are able to grow in animal component free medium in a concentration of less than 100 cells/ml. In a preferred embodiment of the invention the cells of the population of cells are cells which are adapted to grow in an animal component free medium in a concentration of less than 100 cells/ml.

In a preferred embodiment of the invention the method comprises an additional step before step a) wherein the cells of the population of cells are adapted to grow in an animal component free medium. In an alternative embodiment of the invention the cells of the population of cells are adapted to grow in an animal component free medium in step a).

The cells which are adapted to grow in an animal component free medium can also be provided, e.g. by using commercially available cells, to be used in step a).

Suitable methods to adapt cells to grow in an animal component free medium, i.e. to obtain cells which are adapted to grow in an animal component free medium are well known in the state of the art.

In a preferred embodiment of the invention the animal component free medium is a protein free medium.

In a preferred embodiment of the invention the first serum free medium used in step a) contains albumin in a concentration of less than 0.1% per weight. In a preferred embodiment of the invention the first serum free medium used in step a) contains albumin in a concentration of at most 0.09% per weight. In a preferred embodiment of the invention the first serum free medium used in step a) contains albumin in a concentration of at most 0.05% per weight. In a preferred embodiment of the invention the first serum free medium used in step a) contains albumin in a concentration of at most 0.01% per weight.

In a preferred embodiment of the invention the first serum free medium used in step a) contains recombinant albumin in a concentration of less than 0.1% per weight. In a preferred embodiment of the invention the first serum free medium used in step a) contains recombinant albumin in a concentration of at most 0.09% per weight. In a preferred embodiment of the invention the first serum free medium used in step a) contains recombinant albumin in a concentration of at most 0.05% per weight. In a preferred embodiment of the invention the first serum free medium used in step a) contains recombinant albumin in a concentration of at most 0.01% per weight.

In a preferred embodiment of the invention the first serum free medium used in step a) contains transferrin in a concentration of less than 5 µg/ml. In a preferred embodiment of the invention the first serum free medium used in step a) contains transferrin in a concentration of at most 4.9 µg/ml. In a preferred embodiment of the invention the first serum free medium used in step a) contains transferrin in a concentration of at most 4 µg/ml. In a preferred embodiment of the invention the first serum free medium used in step a) contains transferrin in a concentration of at most 1 µg/ml. In a preferred embodiment of the invention the first serum free medium used in step a) contains transferrin in a concentration of at most 0.5 µg/ml.

In a preferred embodiment of the invention the first serum free medium used in step a) contains recombinant transferrin in a concentration of less than 5 µg/ml. In a preferred embodiment of the invention the first serum free medium used in step a) contains recombinant transferrin in a concentration of at most 4.9 µg/ml. In a preferred embodiment of the invention the first serum free medium used in step a) contains recombinant transferrin in a concentration of at most 4 µg/ml. In a preferred embodiment of the invention the first serum free medium used in step a) contains recombinant transferrin in a concentration of at most 1 µg/ml. In a preferred embodiment of the invention the first serum free medium used in step a) contains recombinant transferrin in a concentration of at most 0.5 µg/ml.

In a preferred embodiment of the invention the first serum free medium used in step a) contains no recombinant albumin. In a preferred embodiment of the invention the first serum free medium used in step a) contains no recombinant transferrin. In a preferred embodiment of the invention the first serum free medium used in step a) contains no recombinant albumin and no recombinant transferrin.

In a preferred embodiment of the invention the first serum free medium used in step a) contains no albumin and no transferrin.

In a preferred embodiment of the invention the cell culture medium used in step c) contains more than 2 g/l recombinant albumin. In a preferred embodiment of the invention the cell culture medium used in step c) contains at least 2.1 g/l recombinant albumin. In a preferred embodiment of the invention the cell culture medium used in step c) contains at least 2.5 g/l recombinant albumin. In a preferred embodiment of the invention the cell culture medium used in step c) contains at least 3 g/l recombinant albumin. In a preferred embodiment of the invention the cell culture medium used in step c) contains at least 5 g/l recombinant albumin. In a preferred embodiment of the invention the cell culture medium used in step c) contains at least 10 g/l recombinant albumin. In a preferred embodiment of the invention the cell culture medium used in step c) contains at least 20 g/l recombinant albumin.

In a preferred embodiment of the invention the cell culture medium used in step c) contains more than 10 mg/l recombinant transferrin. In a preferred embodiment of the invention the cell culture medium used in step c) contains at least 10.1 mg/l recombinant transferrin. In a preferred embodiment of the invention the cell culture medium used in step c) contains at least 11 mg/l recombinant transferrin. In a preferred embodiment of the invention the cell culture medium used in step c) contains at least 20 mg/l recombinant transferrin. In a preferred embodiment of the invention the cell culture medium used in step c) contains at least 50 mg/l recombinant transferrin. In a preferred embodiment of the invention the cell culture medium used in step c) contains at least 100 mg/l recombinant transferrin.

In a preferred embodiment of the invention the cell culture medium used in step a) contains less than 2 g/l recombinant albumin and wherein the cell culture medium used in step c) contains more than 2 g/l recombinant albumin. In a preferred embodiment of the invention the cell culture medium used in step a) contains less than 1 g/l recombinant albumin and wherein the cell culture medium used in step c) contains more than 1 g/l recombinant albumin. In a preferred embodiment of the invention the cell culture medium used in step a) contains less than 2 g/l recombinant albumin and wherein the cell culture medium used in step c) contains more than 1 g/l recombinant albumin. In a preferred embodiment of the invention the cell culture medium used in step a) contains less than 1 g/l recombinant albumin and wherein the cell culture medium used in step c) contains more than 2 g/l recombinant albumin. In a preferred embodiment of the invention the cell culture medium used in step a) contains at most 0.5 g/l recombinant albumin and wherein the cell culture medium used in step c) contains at least than 2.5 g/l recombinant albumin.

In a preferred embodiment of the invention the cell culture medium used in step a) contains less than 5 µg/ml recombinant transferrin and wherein the cell culture medium used in step c) contains more than 5 µg/ml recombinant transferrin. In a preferred embodiment of the invention the cell culture medium used in step a) contains less than 10 µg/ml recombinant transferrin and wherein the cell culture medium used in step c) contains more than 10 µg/ml recombinant transferrin. In a preferred embodiment of the invention the cell culture medium used in step a) contains less than 5 µg/ml recombinant transferrin and wherein the cell culture medium used in step c) contains more than 10 µg/ml recombinant transferrin. In a preferred embodiment of the invention the cell culture medium used in step a) contains less than 10 µg/ml recombinant transferrin and wherein the cell culture medium used in step c) contains more than 5 µg/ml recombinant transferrin. In a preferred embodiment of the invention the cell culture medium used in step a) contains at most 4 µg/ml recombinant transferrin and wherein the cell culture medium used in step c) contains at least 6 µg/ml recombinant transferrin.

In a preferred embodiment of the invention the cell culture medium used in step a) contains less than 2 g/l recombinant albumin and less than 5 µg/ml recombinant transferrin and the cell culture medium used in step c) contains more than 2 g/l recombinant albumin more than 5 µg/ml recombinant transferrin. In a preferred embodiment of the invention the cell culture medium used in step a) contains less than 1 g/l recombinant albumin and less than 10 µg/ml recombinant transferrin and wherein the cell culture medium used in step c) contains more than 1 g/l recombinant albumin more than 10 µg/ml recombinant transferrin. In a preferred embodiment of the invention the cell culture medium used in step a) contains less than 1 g/l recombinant albumin and less than 5 µg/ml recombinant transferrin and the cell culture medium used in step c) contains more than 2 g/l recombinant albumin more than 10 µg/ml recombinant transferrin. In a preferred embodiment of the invention the cell culture medium used in step a) contains at most 0.5 g/l recombinant albumin and at most 4 µg/ml recombinant transferrin and the cell culture medium used in step c) contains at least 3 g/l recombinant albumin at least 15 µg/ml recombinant transferrin.

In a preferred embodiment of the invention the cell culture medium used in step a) contains less recombinant albumin, especially albumin, than the cell culture medium used in step c). In a preferred embodiment of the invention the cell culture medium used in step a) contains less recombinant transferrin, especially transferrin, than the cell culture medium used in step c). In a preferred embodiment of the invention the cell culture medium used in step a) contains less recombinant albumin, especially albumin, and less recombinant transferrin, especially transferrin, than the cell culture medium used in step c).

In a preferred embodiment of the invention the cell culture medium used in step a) is an animal component free medium, more preferably a protein free medium. In a preferred embodiment of the invention the cell culture medium used in step c) is an animal component free medium.

In a preferred embodiment of the invention, the method comprises additionally the step d) culturing the cells in a third serum free cell culture medium which has a lower concentration of recombinant transferrin and/or recombinant albumin than the cell culture medium of step c). In a preferred embodiment of the invention, the method comprises additionally the step d) culturing the cells in a third serum free cell culture medium which has a lower concentration of recombinant transferrin and recombinant albumin than the cell culture medium of step c). In a preferred embodiment of the invention, the method comprises additionally the step d) culturing the cells in a third serum free cell culture medium which has a lower concentration of recombinant transferrin than the cell culture medium of step c). In a preferred embodiment of the invention, the method comprises additionally the step d) culturing the cells in a third serum free cell culture medium which has a lower concentration of recombinant albumin than the cell culture medium of step c).

In a preferred embodiment of the invention, the method comprises additionally the step d) culturing the cells in a third serum free cell culture medium which has concentration of recombinant transferrin and of recombinant albumin which is 80% or lower, preferably 50% or lower, than the concentration of recombinant transferrin and of recombinant albumin in the cell culture medium of step c).

In a preferred embodiment of the invention, the method comprises additionally the step d) culturing the cells in a third serum free cell culture medium which has an at least two-fold lower concentration of recombinant transferrin and an at least two-fold lower concentration of recombinant albumin than the cell culture medium of step c).

According to the preferred embodiment the step d) follows step c).

In a preferred embodiment of the invention the cell culture medium of step d) is free of recombinant transferrin and recombinant albumin.

In a preferred embodiment of the invention the serum free cell culture medium is an animal component free cell culture medium. In a preferred embodiment of the invention the serum free cell culture medium is a protein free cell culture medium.

In a preferred embodiment of the invention the serum free cell culture medium of step a) is an animal component free cell culture medium. In a preferred embodiment of the invention the serum free cell culture medium of step a) is a protein free cell culture medium.

In a preferred embodiment of the invention the serum free cell culture medium of step c) is an animal component free cell culture medium. In a preferred embodiment of the invention the serum free cell culture medium of step c) is a protein free cell culture medium.

In a preferred embodiment of the invention the serum free cell culture medium of step d) is an animal component free cell culture medium. In a preferred embodiment of the invention the serum free cell culture medium of step d) is a protein free cell culture medium.

In a preferred embodiment of the invention the cell culture medium of step c) has an osmolality between 280 and 320 mOsmol/kg $H_2O$.

In a preferred embodiment of the invention the cell culture medium of step c) has an osmolality between 280 and 300 mOsmol/kg $H_2O$. In a preferred embodiment of the invention the cell culture medium of step c) has a pH between 6.0 and 8.0. In a preferred embodiment of the invention the cell culture medium of step c) has a pH between 6.8 and 7.1.

In a preferred embodiment of the invention the cell culture medium of step c) has an osmolality between 280 and 320 mOsmol/kg $H_2O$ and a pH between 6.8 and 7.1.

In a preferred embodiment of the invention the cell culture medium of step c) has an osmolality between 280 and 300 mOsmol/kg $H_2O$ and a pH between 6.8 and 7.0. In a preferred embodiment of the invention the cell culture medium used in step a) and/or c), and/or d) contains L-glutamine. In a preferred embodiment of the invention the cell culture medium used in step a) and/or c), and/or d) contains L-glutamine in a concentration lower than 6 mM. In a preferred embodiment of the invention the cell culture medium used in step a) and/or c), and/or d) contains L-glutamine in a concentration lower than 4 mM. In a preferred embodiment of the invention the cell culture medium used in step a) and/or c), and/or d) contains L-glutamine in a concentration lower than 2 mM. In a preferred embodiment of the invention the cell culture medium used in step a) and/or c), and or d) does not contain L-glutamine.

In a preferred embodiment of the invention the cell culture medium contains L-glutamine. In a preferred embodiment of the invention the cell culture medium used in step c) contains L-glutamine. In a preferred embodiment of the invention the cell culture medium used in step d) contains L-glutamine. In a preferred embodiment of the invention the cell culture media used in steps a) and c) contain L-glutamine. In a preferred embodiment of the invention the cell culture media used in steps a), c) and d) contain L-glutamine.

In a preferred embodiment of the invention the cell culture medium used in step a) contains L-glutamine in a concentration lower than 50 mM. In a preferred embodiment of the invention the cell culture medium used in step c) contains L-glutamine in a concentration lower than 50 mM. In a preferred embodiment of the invention the cell culture medium used in step d) contains L-glutamine in a concentration lower than 50 mM.

In a preferred embodiment of the invention the cell culture medium used in step a) contains L-glutamine in a concentration lower than 6 mM. In a preferred embodiment of the invention the cell culture medium used in step c) contains L-glutamine in a concentration lower than 6 mM. In a preferred embodiment of the invention the cell culture medium used in step d) contains L-glutamine in a concentration lower than 6 mM.

In a preferred embodiment of the invention the cell culture medium used in step a) contains L-glutamine in a concentration lower than 4 mM. In a preferred embodiment of the invention the cell culture medium used in step c) contains L-glutamine in a concentration lower than 4 mM. In a preferred embodiment of the invention the cell culture medium used in step d) contains L-glutamine in a concentration lower than 4 mM.

In a preferred embodiment of the invention the cell culture media used in steps a) and c) contain L-glutamine in a concentration lower than 50 mM. In a preferred embodiment of the invention the cell culture media used in steps a) and c) contain L-glutamine in a concentration lower than 6 mM. In a preferred embodiment of the invention the cell culture media used in steps a) and c) contain L-glutamine in a concentration lower than 4 mM. In a preferred embodiment of the invention the cell culture media used in steps a), c) and d) contain L-glutamine in a concentration lower than 4 mM.

In a preferred embodiment of the invention all cell culture media used contain L-glutamine in the same concentration. In a preferred embodiment of the invention all cell culture media used contain L-glutamine in a concentration of lower than 50 mM. In a preferred embodiment of the invention all cell culture media used contain L-glutamine in a concentration of lower than 20 mM. In a preferred embodiment of the invention all cell culture media used contain L-glutamine in a concentration of lower than 6 mM. In a preferred embodiment of the invention all cell culture media used contain L-glutamine in a concentration of lower than 4 mM. In a preferred embodiment of the invention the cell culture media used in steps a) and/or c) contain iron. In a preferred embodiment of the invention the cell culture media used in steps a) and/or c) and/or d) contain iron.

In a preferred embodiment of the invention the cell culture medium used in step a) contains iron. In a preferred embodiment of the invention the cell culture medium used in step c) contains iron. In a preferred embodiment of the invention the cell culture medium used in step d) contains iron. In a preferred embodiment of the invention the cell culture media used in steps a) and c) contain iron.

In a preferred embodiment of the invention the cell culture medium used in step a) contains a non-transferrin bound iron. In a preferred embodiment of the invention the cell culture medium used in step c) contains a non-transferrin bound iron. In a preferred embodiment of the invention the cell culture medium used in step d) contains a non-transferrin bound iron.

In a preferred embodiment of the invention the cell culture media used in steps a) and/or c) contain a non-transferrin bound iron. In a preferred embodiment of the invention the cell culture media used in steps a) and/or c) and/or d) contain a non-transferrin bound iron.

In a preferred embodiment of the invention the cell culture media used in steps a) and c) contain a non-transferrin bound iron. In a preferred embodiment of the invention the cell culture media used in steps a), c) and d) contain a non-transferrin bound iron.

In a preferred embodiment of the invention the cells are cultured in step a) for at least 1 day without sub-culturing the cells. In a preferred embodiment of the invention the cells are cultured in step a) for at least 2 days without sub-culturing the cells. In a preferred embodiment of the invention the cells are cultured in step a) at least 3 days without sub-culturing the cells.

In a preferred embodiment of the invention the cells are cultured in step c) for at least 5 days. In a preferred embodiment of the invention the cells are cultured in step c) for at least 10 days. In a preferred embodiment of the invention the cells are cultured in step c) for at least 5 days without sub-culturing the cells. In a preferred embodiment of the invention the cells are cultured in step c) for at least 10 days without sub-culturing the cells.

In a preferred embodiment of the invention the cells are cultured in step d) for at least 3 days. In a preferred embodiment of the invention the cells are cultured in step d) for at least 6 days.

In a preferred embodiment of the invention the cells are cultured in step d) for at least 3 days without sub-culturing the cells. In a preferred embodiment of the invention the cells are cultured in step d) for at least 6 days without sub-culturing the cells.

In a preferred embodiment of the invention the cells are cultured in steps c) and d) together for at least 3 days. In a preferred embodiment of the invention the cells are cultured in steps c) and d) together for at least 6 days.

In a preferred embodiment of the invention the cells are cultured in steps c) and d) together for at least 3 days without sub-culturing the cells. In a preferred embodiment of the invention the cells are cultured in steps c) and d) together for at least 6 days without sub-culturing the cells.

In a preferred embodiment of the invention the culture volume in step a) is 0.1 ml, more preferred 0.5 ml, more preferred 3 ml, more preferred 15 ml, more preferred 100 ml.

In a preferred embodiment of the invention the culture volume in step a) is at least 0.1 ml. In a preferred embodiment of the invention the culture volume in step a) is at least 0.5 ml. In a preferred embodiment of the invention the culture volume in step a) is at least 3 ml. In a preferred embodiment of the invention the culture volume in step a) is about 3 ml. In a preferred embodiment of the invention the culture volume in step a) is at least 15 ml. In a preferred embodiment of the invention the culture volume in step a) is about 15 ml. In a preferred embodiment of the invention the culture volume in step a) is at least 100 ml. In a preferred embodiment of the invention the culture volume in step a) is about 100 ml. In a preferred embodiment of the invention the culture volume in step a) is at most 1 l. In a preferred embodiment of the invention the culture volume in step a) is at most 0.5 l.

In a preferred embodiment of the invention the culture volume in step c) is at most about 5 ml. In a preferred embodiment of the invention the culture volume in step c) is at most 2 ml. In a preferred embodiment of the invention the culture volume in step c) is at most about 2 ml. In a preferred embodiment of the invention the culture volume in step c) is at most about 1 ml. In a preferred embodiment of the invention the culture volume in step c) is at most 450 µl. In a preferred embodiment of the invention the culture volume in step c) is at most 150 µl. In a preferred embodiment of the invention the culture volume in step c) is at most 100 µl. In a preferred embodiment of the invention the culture volume in step c) is at most about 100 µl. In a preferred embodiment of the invention the culture volume in step c) is 30 µl. In a preferred embodiment of the invention the culture volume in step c) is at most 10 µl. In a preferred embodiment of the invention the culture volume in step c) is at most about 10 µl.

In a preferred embodiment of the invention the culture volume in step c) is at least 1 µl. In a preferred embodiment of the invention the culture volume in step c) is at least 5 µl. In a preferred embodiment of the invention the culture volume in step c) is at least about 5 µl. In a preferred embodiment of the invention the culture volume in step c) is at least about 10 µl. In a preferred embodiment of the invention the culture volume in step c) is at least 100 µl. In a preferred embodiment of the invention the culture volume in step c) is at least about 100 µl. In a preferred embodiment of the invention the culture volume in step c) is at least about 0.5 ml. In a preferred embodiment of the invention the culture volume in step c) is at least 0.5 ml. In a preferred embodiment of the invention the culture volume in step c) is at least about 1 ml. In a preferred embodiment of the invention the culture volume in step d) is at most 20 µl. In a preferred embodiment of the invention the culture volume in step d) is at most 60 µl. In a preferred embodiment of the invention the culture volume in step d) is at most 200 µl. In a preferred embodiment of the invention the culture volume in step d) is at most 600 µl. In a preferred embodiment of the invention the culture volume in step d) is 1.8 ml. In a preferred embodiment of the invention the culture volume in step d) is at most 5 ml.

In a preferred embodiment of the invention the culture volume in step d) is at least 1 µl. In a preferred embodiment of the invention the culture volume in step d) is at least about 1 µl. In a preferred embodiment of the invention the culture volume in step d) is at least 10 µl. In a preferred embodiment of the invention the culture volume in step d) is at least about 10 µl. In a preferred embodiment of the invention the culture volume in step d) is at least 50 µl. In a preferred embodiment of the invention the culture volume in step d) is at least 100 µl. In a preferred embodiment of the invention the culture volume in step d) is at least 300 µl. In a preferred embodiment of the invention the culture volume in step d) is at least about 1.5 ml. In a preferred embodiment of the invention the culture volume in step d) is at least about 3 ml. In a preferred embodiment of the invention the culture volume in step d) is at least 3 ml. In a preferred embodiment of the invention the cell culture medium used in step c) contains at least 50 mg/l recombinant albumin. In a preferred embodiment of the invention the cell culture medium used in step c) contains at least 200 mg/l recombinant albumin. In a preferred embodiment of the invention the cell culture medium used in step c) contains at least 1000 mg/l recombinant albumin. In a preferred embodiment of the invention the cell culture medium used in step c) contains at least 2000 mg/l recombinant albumin. In a preferred embodiment of the invention the cell culture medium used in step c) contains at least 5000 mg/l recombinant albumin. In a preferred embodiment of the invention the cell culture medium used in step c) contains at most 50000 mg/l recombinant albumin. In a preferred embodiment of the invention the cell culture medium used in step c) contains at least 0.1 mg/l recombinant transferrin. In a preferred embodiment of the invention the cell culture medium used in step c) contains at least 1 mg/l recombinant transferrin. In a preferred embodiment of the invention the cell culture medium used in step c) contains at least 5 mg/l recombinant transferrin. In a preferred embodiment of the invention the cell culture medium used in step c) contains at least 50 mg/l recombinant transferrin. In a preferred embodiment of the invention the cell culture medium used in step c) contains at least 250 mg/l recombinant transferrin. In a preferred embodiment of the invention the cell culture medium used in step c) contains at most 2500 mg/l recombinant transferrin. In a preferred embodiment of the invention the cell culture medium used in step c) contains at least 50 mg/l recombinant albumin and at least 0.1 mg/l recombinant transferrin. In a preferred embodiment of the invention the cell culture medium used in step c) contains at least 1000 mg/l recombinant albumin and at least 1 mg/l recombinant transferrin. In a preferred embodiment of the invention the cell culture medium used in step c) contains at least 2000 mg/l recombinant albumin and at least 5 mg/l recombinant transferrin. In a preferred embodiment of the invention the cell culture medium used in step c) contains at least 5000 mg/l recombinant albumin and at least 50 mg/l recombinant transferrin.

In a preferred embodiment of the invention the cell culture medium used in step d) contains less than 5000 mg/l recombinant albumin. In a preferred embodiment of the invention the cell culture medium used in step d) contains less than 50 mg/l recombinant transferrin.

In a preferred embodiment of the invention the cell culture medium used in step d) contains less than 5000 mg/l recombinant albumin and less than 50 mg/l recombinant transferrin. In a preferred embodiment of the invention the cell culture medium used in step d) contains less than 2000 mg/l recombinant albumin and less than 5 mg/l recombinant transferrin. In a preferred embodiment of the invention the cell culture medium used in step d) contains less than 50 mg/l recombinant albumin and less than 0.1 mg/l recombinant transferrin. In a preferred embodiment of the invention the cell culture medium used in step d) does not contain recombinant albumin and does not contain recombinant transferrin.

In a preferred embodiment of the invention the cell culture medium used in step a) is an animal component free culture medium. In a preferred embodiment of the invention the cell culture medium used in step c) is an animal component free culture medium. In a preferred embodiment of the invention the cell culture medium used in step d) is an animal component free culture medium.

In a preferred embodiment of the invention the cell culture media used in steps a) and c) are animal component free culture media. In a preferred embodiment of the invention the cell culture media used in steps c) and d) are animal component free culture media. In a preferred embodiment of the invention the cell culture media used in steps a), c) and d) are animal component free culture media.

In a preferred embodiment of the invention all cell culture media used are animal component free cell culture media. In a preferred embodiment of the invention the cell population is reduced in step b) by an automatic cell sorting system.

In a preferred embodiment of the invention the single cell is isolated in step b) by an automatic cell sorting system. In a preferred embodiment of the invention the single cell is isolated in step b) by FACS.

In a preferred embodiment of the invention the cells of the population of cells contain no feeder cells.

In a preferred embodiment of the invention the cells of the population of cells are eukaryotic cells. In a preferred embodiment of the invention the cells of the population of cells are mammalian cells. In a preferred embodiment of the invention the cells of the population of cells are human cells. In a preferred embodiment of the invention the cells of the population of cells are animal cells. In a preferred embodiment of the invention the cells of the population of cells are not human embryonic stem cells.

In a preferred embodiment of the invention the population of cells is a cell line. In a preferred embodiment of the invention the population of cells is a CHO cell line, a NS0 cell line, a Per.C6 cell line, a HEK293 cell line or a BHK cell line. In a preferred embodiment of the invention the population of cells is a CHO cell line. In a preferred embodiment of the invention the population of cells is a cell line. In a preferred embodiment of the invention the population of cells is a NS0 cell line. In a preferred embodiment of the invention the population of cells is a cell line. In a preferred embodiment of the invention the population of cells is a Per.C6 cell line. In a preferred embodiment of the invention the population of cells is a cell line. In a preferred embodiment of the invention the population of cells is a HEK293 cell line. In a preferred embodiment of the invention the population of cells is a cell line. In a preferred embodiment of the invention the population of cells is a BHK cell line. In a preferred embodiment of the invention the cells of the population of cells are prokaryotic cells.

The present invention relates also in a preferred embodiment to the use of a serum free cell culture medium containing recombinant albumin and recombinant transferrin for the cultivation of a population of cells with a cell concentration of less than about 100 cells/ml. The present invention relates also in a preferred embodiment to the use of a serum free cell culture medium containing recombinant albumin and recombinant transferrin for the cultivation of a population of cells with a cell concentration of less than 100 cells/ml.

The present invention relates also in a preferred embodiment to the use of a serum free cell culture medium containing recombinant albumin and recombinant transferrin for the cultivation of a single cell.

The preferred embodiments concerning the method according to the present invention are also preferred embodiments for the use according to the present invention.

The present invention relates also in a preferred embodiment to a cell population with a cell concentration of less than about 100 cells/ml cultivated in a serum free cell culture medium containing recombinant albumin and recombinant transferrin.

The present invention relates also in a preferred embodiment to a cell population with a cell concentration of less than 100 cells/ml cultivated in a serum free cell culture medium containing recombinant albumin and recombinant transferrin.

The present invention relates also in a preferred embodiment to a single cell cultivated in a serum free cell culture medium containing recombinant albumin and recombinant transferrin. The preferred embodiments concerning the method according to the present invention are also preferred embodiments for the cell population in a serum free cell culture medium containing recombinant albumin and recombinant transferrin according to the present invention.

The here presented invention is a serum free culture medium for single cell cloning containing recombinant albumin and recombinant transferrin. The experiments were performed with CHO cell lines already adapted to grow in a culture medium free of serum, growth factors, proteins, and peptones. The culture medium contains an inorganic iron source. In this culture media the cell line reaches a cell concentration up to $3 \times 10^7$ cells/ml in a fed-batch process. This demonstrates a very good growth independently from serum and protein additives. However, the efficacy of the clonal growth of the same cells in single cell status in the same medium was very low.

Surprisingly we have found that clonal growth of the cell line can be significantly enhanced by addition of recombinant proteins. It turned out that cell lines have different demands on culture media when grown in single cell status as compared to growth in a population of cells. A person skilled in the art would think that a serum and protein independent growing cell line should also clonally grow in a milieu free of serum and proteins. We were surprised to find out, that the same cell line has different requirements on media when cultured in a single cell state and in a cell population.

Accordingly, it is surprisingly only necessary that recombinant albumin and/or recombinant transferrin is present in step c). The cells do not need recombinant albumin and/or recombinant transferrin before and after step c), at least in high concentrations.

According to our invention, a cell line will be contacted with a culture medium containing recombinant albumin and recombinant transferrin, when the clonal cell growth is required. Apparently recombinant albumin and recombinant transferrin have a synergistic effect on cells. Both proteins were also tested separately. They promote the cell proliferation each at a low level. When both proteins were combined, cell growth and viability of single cells is significantly increased almost at the levels of serum containing control cultures or even higher than serum containing control cultures.

We have further examined if additional parameters of the culture media plays a role in improving the clonal growth. To our surprise we have found, that single cells have different requirements also regarding the culture media osmolality and culture media pH. The clonal growth can be even more improved when the osmolality of the culture medium is lowered. Preferred osmolality of the culture medium is between 260 and 360 mOsmol/kg $H_2O$, more preferred 270 to 340, more preferred 280 to 320, more preferred 290 to 300 mOsmol/kg $H_2O$. The clonal growth can be even more improved when the pH of the culture medium is lower than usual in culture media. Preferred culture medium pH is between 6.7 and 7.3, more preferred 6.8 and 7.2, more preferred 6.8 and 7.0.

Recombinant proteins as media additives are expensive. It is therefore, interesting omitting the recombinant proteins in culture media. According to a preferred embodiment of the invention an easy and cost efficient way of promoting the clonal growth is in a first step culturing cells in a medium containing low concentration of recombinant albumin and recombinant transferrin or culturing cells in a medium which is free of recombinant albumin and recombinant transferrin. In a second step the cells are contacted with a culture medium containing recombinant albumin and recombinant transferrin at higher concentration than applied in the first step. In step three the cells can be cultured in a culture medium with lower concentration of recombinant albumin and recombinant transferrin or recombinant albumin and recombinant transferrin can be completely omitted. Through this procedure practically, the recombinant albumin and recombinant transferrin can be applied only by reduced cell concentration or in single cell cloning step and in all other cell culturing steps the expensive recombinant proteins can be omitted and a cost efficient and easy method can be established for single cell cloning.

Another main advantage of the method according to the invention is that cells can be cultured through out all steps in animal component free culture media, which has great advantage for regulatory authorities by production of therapeutic proteins.

The term "recombinant protein" refers to a protein that is encoded by a nucleic acid that is introduced into a host cell. The host cell expresses the nucleic acid. "Protein" as used herein broadly refers to polymerised amino acids, e.g. peptides, polypeptides, protein, Upon proteins, glycoproteins, etc.

The term "serum free medium" or "serum free cell culture medium" is a medium that contains no serum from any organism (e.g. fetal bovine serum (FBS), calf serum, horse serum, goat serum, human serum, etc.).

The term "cell culture" or "culture" is meant the maintenance of cells in an artificial, in vitro environment, it is to be understood, however, that the term "cell culture" is a generic term and may be used to encompass the cultivation not only of individual cells or only single cell or only a cell population, but also of tissues or organs, for which the terms "tissue culture" or "organ culture", may occasionally be used interchangeably with the term "cell culture".

The term "contacting" refers to the placing of cells to be cultivated in vitro into a culture vessel with the medium in which the cells are to be cultivated. The term "contacting" encompasses mixing cells with a medium, pipetting medium onto cells in a culture vessel, and submerging cells in a culture medium.

The term "albumin" refers to a protein which is an abundant protein contained in plasma. It contributes to the maintenance of osmotic pressure in blood and probably binds to nutrients to transport these substances to cells. Different versions of albumin exists, for example but not limited to human serum albumin (HSA), bovine serum albumin (BSA), a fraction or a part of HSA, a fraction or a part of BSA. Albumin might be further any protein or polypeptide which gives substantially similar results in terms of cell growth, cell viability or cellular productivity regarding osmolality regulation of medium and regarding nutrient binding or nutrient transfer to cells. Preferably the albumin is of human origin. Most preferably the albumin is human serum albumin. Even more preferably the albumin is recombinantly produced human serum albumin ("recombinant HSA"). The recombinant HSA can be produced in divers organisms, like prokaryotic or eukaryotic cells, e.g. bacteria, plant or yeast, etc. The production of recombinant albumin is known in the art in numerous hosts e.g. *E. coli* (EP73646) and fungal cell (WO0044772). For example but not limited to the recombinant albumin is a human recombinant albumin as stated out by SIGMA™ (A7223).

The term "transferrin" refers to any biological compound which has iron binding or chelating abilities. Examples of transferrin include but are not limited to any protein, polypeptide or peptide which has an affinity to iron, for example iron binding or chelating abilities. Other examples of transferrin include but are not limited are proteins, polypeptides or peptides which have any affinity to cellular transferrin receptor. Such proteins, polypeptides or peptides can recognise, bind partly, or bind fully the cellular transferrin receptor. Transferrin can be saturated with iron or not. If transferrin is not saturated with iron, the culture media might contain inorganic iron. If transferrin is saturated with iron the culture media can be free of inorganic iron or the culture media can contain additionally inorganic iron. Preferably transferrin is saturated with iron. More preferably, transferrin is iron saturated human transferrin.

The term "recombinant transferrin" is the transferrin which is recombinantly produced in any organism. The recombinant transferrin can be produced in divers organisms, like prokaryotic or eukaryotic cells. Recombinant transferrin can be produced in bacteria, plant, fungi or yeast. Preferred is the recombinantly produced human transferrin. For example but not limited to recombinant human transferrin is the recombinant human transferrin from MILLIPORE™ (9701-10) as described in the product specification.

The present invention relates in a particularly preferred embodiment to a culture medium, wherein the recombinant albumin is contained therein in a concentration of at least, preferably more than 0.1 g/l, at least preferably more than 0.2 g/l, at least preferably more than 0.5 g/l, at least preferably more than 1.0 g/l, at least preferably more than 2 g/l, or in a particularly preferred embodiment at least preferably more than 3 g/l, or in a further particularly preferred embodiment at least preferably more than 5 g/l. In a further preferred embodiment, the present invention provides a culture medium according to the above, wherein the concentration of the recombinant transferrin is at least, preferably more than 0.1 mg/l, at least preferably more than 1 mg/l, at least preferably more than 2 mg/l, at least preferably more than 4 mg/l, at least preferably more than 6 mg/l, at least preferably more than 8 mg/l, at least preferably more than 10 mg/l, at least preferably more than 20 mg/l, at least preferably more than 50 mg/l, at least preferably more than 200 mg/l, or in a particularly preferred embodiment at least, preferably more than, 1000 mg/l.

The term "animal component free" refers to a culture medium or to a cell culture process, in which no components are used, which are originated from an animal or from a human.

The term "sufficient to support the growth of a single cell" means that the culture media are capable of supporting growth of a single cell, but does not require that the media actually be used to support growth of a single cell. The media can be applied for the growth of a single cell or for the growth of a cell population at a concentration of lower than 100 cells/ml or for the growth of a cell population at a cell concentration higher than 100 cells/ml. The media of the present invention is contacted with a population of cells, in growth conditions capable of sustaining clonal growth, that is, growth at very low cell densities, such as densities less then about 100 cells/ml, including single cells.

The term "cell culture medium", "tissue culture medium", "culture medium", "stock culture medium" "cloning medium" (plural "media" in each case) refers to a nutritive solution for cultivating cells or tissues, and may be used interchangeably. A culture medium is a medium which is suitable for cultivation or for incubation of a cell or several cells. Such culture media may contain nutrients for keeping the cell integrity or cell viability or cell growth or cellular productivity. Preferred is a liquid culture medium. A particularly preferred culture medium is described in WO 2007/036291 and may be used for the present invention. A particularly preferred culture medium contains all necessary substances for cell growth, cell viability and cellular productivity. A preferred culture medium in particular may contain for example and not being limited to glucose, amino acids, salts, trace elements and fatty acids.

The cell culture of mammalian cells is nowadays a routine operation well-described in scientific textbooks and manuals. It is covered in detail e.g. in R. Ian Fresney, Culture of Animal cells, a manual, $4^{th}$ edition, Wiley-Liss/N.Y., 2000. Culture media and culture methods, for instance for mammalian cell lines, for use in combination with the culture additives of the present invention are per se well-known in the art. Such culture media are preferably composed of a solvent, such as water, a carbon source, a nitrogen source, amino acids, pH regulators, trace elements, fatty acids, nucleotides. Preferred culture media for the present invention are standard cell culture media, which may also be adapted to the needs of particular cell types and include, without being restricted to, Roswell Park Memorial Institute (RPMI) 1640 medium, L-15 medium, Dulbecco's modified Eagle's medium (DMEM), Eagle's minimal essential medium (MEM), Ham's F12 medium or Iscoves' modified DMEM. Other preferred media are for instance, Ham's F10 or F12 media, which are specially designed for CHO cell culture. Other preferred media for the present invention are specially adapted to CHO cell culture and are described for instance in EP 0 481 791. A preferred culture medium for the present invention can also be a commercially available medium, for example, but not limited to CD CHO (GIBCO®, 10743), PROCHO™5 (BIOWHITTAKER®, BE12-766Q), HYQSFM4™-CHO (HYCLONE™, SH30548.02).

In a further preferred embodiment of the present invention the culture media can contain L-glutamine, glutamine can be fully or partly replaced with glutamine substitutes, e.g. GLUTAMAX™ (GIBCO® Cat.Nr: 35050-061). In a further preferred embodiment of the present invention the culture media can contain low concentration of L-glutamine. The concentration of L-glutamine can be maximal 900 mg/l, preferred 600 mg/l, more preferred 300 mg/l, more preferred 100 mg/l, more preferred 50 mg/l, more preferred 20 mg/l. The culture media can be free of L-glutamine. When the culture medium is free of L-glutamine, then it is particularly suitable for application of cells transfected with glutamine synthetase selection gene.

In a further preferred embodiment of the present invention the culture media contain at least one carbohydrate source. Preferred is the application of glucose in a concentration 0-10 g/l. The glucose can be fully or partly substituted with other carbohydrates for example but not limited to fructose, mannose, galactose.

In a further preferred embodiment of the present invention the culture media can be free of any inorganic iron source and/or free of any iron chelating compounds.

Preferred culture media of the present invention may alternatively in one embodiment also contain hydrolysates from animal source, from plant source or from yeast. Preferred is a hydrolysate from plant source, e.g. soy bean peptone or yeast hydrolysate.

In a particular preferred embodiment, the culture media of the present invention are serum-free. In a particular preferred embodiment, the culture media of the present invention are free of products isolated directly or indirectly from an animal source. In a particularly preferred embodiment of the present invention, the culture media are animal component free. In a particularly preferred embodiment of the present invention, the culture medium is free of hydrolysates.

In a further preferred embodiment of the present invention the culture media can contain inorganic iron.

In a further preferred embodiment of the present invention the culture media can contain one or more iron chelating compounds.

The term "iron" is meant to identify the transition metal Fe with atomic weight of 55,845. The term iron is the generic term which comprises all molecules containing one or more iron ions for example $Fe^{3+}$ and/or $Fe^{2+}$ ions. The $Fe^{3+}$ and/or $Fe^{2+}$ ion can occur in form of an iron salt. Iron salts can be hydrated or dehydrated. In a particularly preferred embodiment, the iron source contains Fe (II) and/or Fe (III) ions. In a particularly preferred embodiment, the iron source for use in the present invention is selected from the group consisting of iron (III) phosphate, iron (III) pyrophosphate, iron (III) nitrate, iron (II) sulphate, iron (III) chloride, iron (II) lactate, iron (III) citrate, ammonium iron (III) citrate, iron-dextran and ethylenediaminetetraacetic acid ferric sodium salt or hydrated or dehydrated forms thereof.

The iron can also be complexed with another molecule, e.g. with a carrier or with a chelator. Some particularly preferred examples of complexed iron with chelators not being limited to are iron (II) lactate hydrate, iron (III) citrate, ammonium iron (III) citrate, iron-dextran and ethylenediaminetetraacetic acid ferric sodium salt. The iron may alternatively also be complexed with the following additional molecules such as described in U.S. Pat. No. 6,048,728, i.e. pyridoxyl isonicotinoyl hydrazone, citrate, acetylacetonate, and a variety of other organic acids such as malic acid, succinic acid, fumaric acid, and alpha ketoglutaric acid. Further iron chelators for use in the present invention are given in WO 2001/016294.

The present invention is not limited to any type of cells. Examples of cell types include mammalian cells, insect cells, bacterial cells, and yeast cells. The cells can also be primary cells or stem cells. The cells may be naturally occurring cells being not transformed or transfected. The cells can also be recombinant cells transfected of transformed with one or more vectors for recombinant gene expression. The cells can be transformed with a virus for producing any product, for example viral products. The cells can originate from hamster, mouse, human or any other animal. The cells can also be cell lines, for example but not limited to CHO cells, CHO K1 cells, CHO DUKX cells, CHO DG44 cells, NS0 cells, Per.C6 cells, BHK cells, SP2/0 cells, HEK293 cells.

Further preferred embodiments of the present invention are the subject-matter of the sub-claims.

The following examples and the accompanying figures describe the present invention in more detail.

FIG. 1 demonstrates the comparison of the cloning efficiency in conditioned medium and rHSA.

Figure 2:
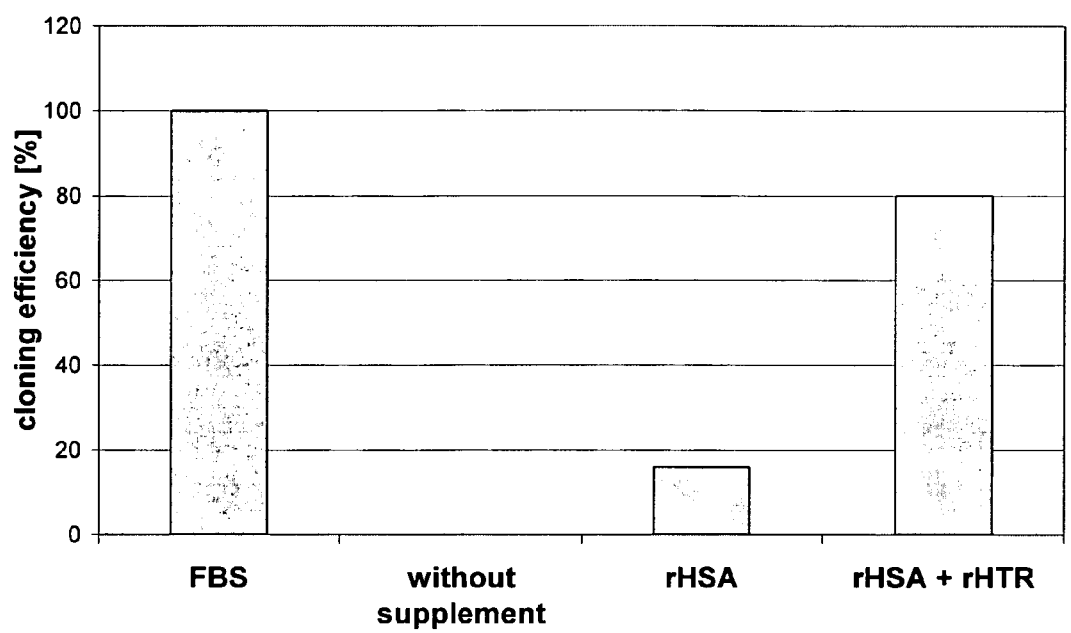

FIG. 2 demonstrates comparison of the cloning efficiency using recombinant human serum albumin with and without addition of recombinant human transferrin.

Figure 3:
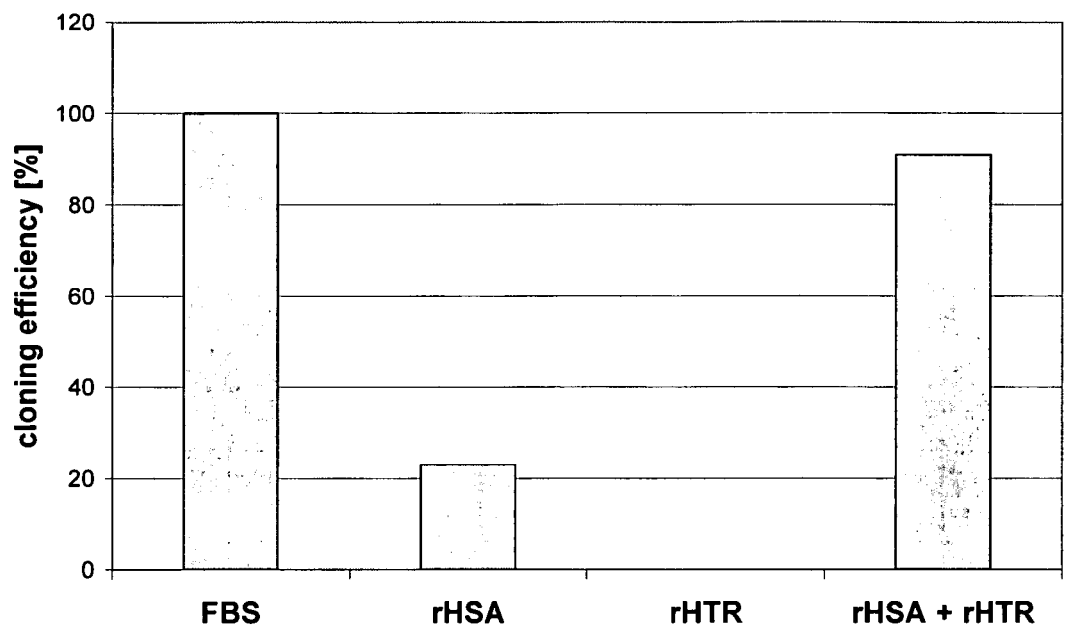

FIG. 3 demonstrates the comparison of the cloning efficiency using rHSA and rHTR separately and in combination.

Figure 4:
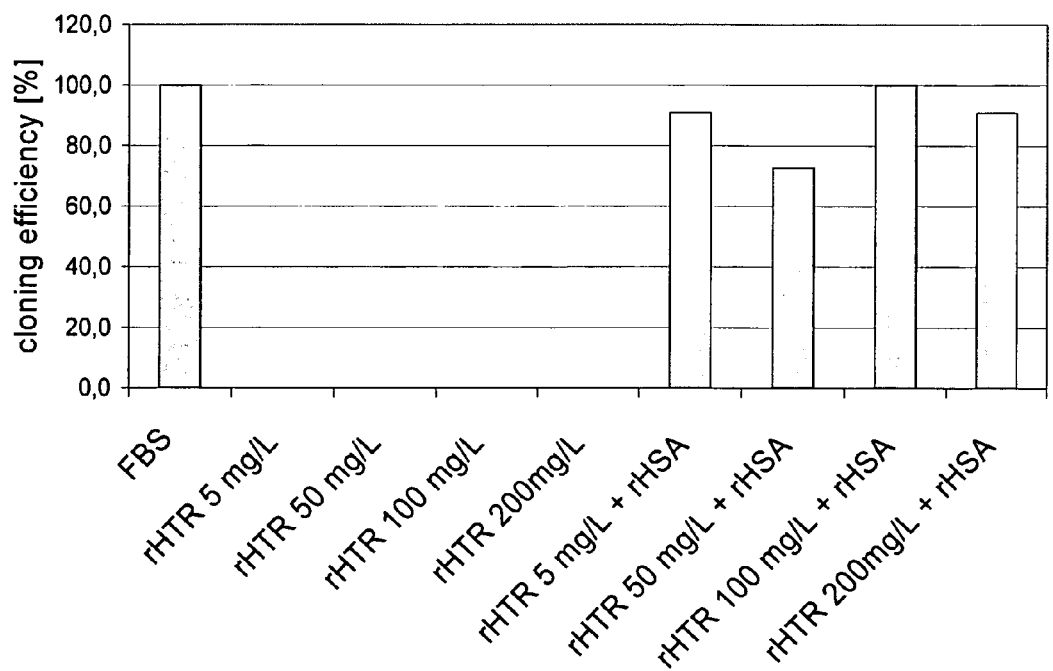

FIG. 4 demonstrates the titration of recombinant human transferrin with and without addition of recombinant human serum albumin and the resulting cloning efficiency.

Figure 5:
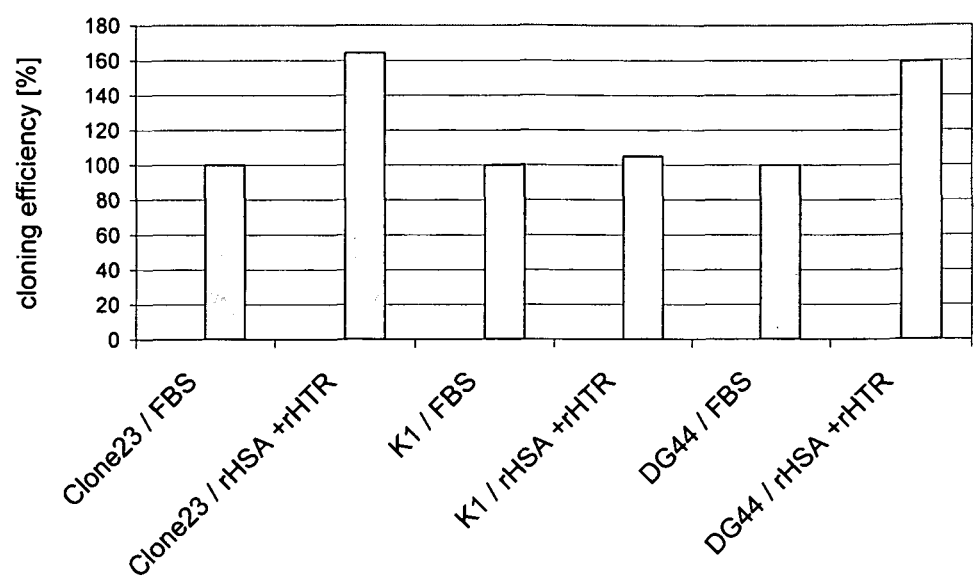

FIG. 5 demonstrates the effect of the combined addition of rHSA and rHTR for promoting cell growth of single cells deposited by FACS. Additionally, these results show the effectiveness of this medium formulation for different CHO cell lines.

EXAMPLES

Cells

For all experiments following three CHO cell lines were used:
1) DHFR (dihydrofolate reductase) deficient CHO DG44 host cell line (Urlaub and Chasin, Proc. Natl. Acad. Sci., 1980, 77: 4216).
2) A transfected CHO DG44 sub clone (named clone23) generated from the cell line mentioned in 1) while expressing DHFR and a recombinant monoclonal antibody. This clone was generated by transfection of the CHO DG44 host cell line with a vector carrying the gene for DHFR and for an IgG antibody. Transfectants were amplified using MTX in culture medium.
3) CHO K1 host cell line (Puck T T, et al., J. Exp. Med., 1958, 108: 945-956). All applied cells in this invention do not require any protein in culture media for growth and viability. All cell lines grow independently of serum, proteins, growth factors, hydrolysates, albumin and transferrin.

Cell Culture Conditions

Stock culture cells used for single cell cloning were kept in shake flasks or in spinner flasks. Cells were inoculated with a cell concentration of $3 \times 10^5$ cells/ml in a shake flask and after growth phase of 2 to 4 days in batch, they reach a cell concentration of $5 \times 10^5$ cells/ml to $100 \times 10^5$ cells/ml. The stock culture was split into fresh culture medium every two to four days. This means, a small amount of cell culture was used as inoculum and transferred into a new flask and supplemented with fresh culture medium. When cells have not reached high concentration, they were centrifuged during cell split. Cells were cultured at 37° C. in a 7.5% $CO_2$ atmosphere in an incubator. Cells were cultured several passages in this way. One passage is defined as culture duration of 2-4 days. Cells for single cell cloning experiments were taken from these stock cultures from exponential growth phase.

Culture Media

Stock Culture Medium

Two different stock culture media were used during the experiments. First, a commercially available stock culture medium with unknown recipe (CD CHO, GIBCO®, 10743) and second a proprietary stock culture medium with following characteristics: The proprietary stock culture medium contains all necessary substances for cell growth, cell viability and cellular productivity, such as but not limited to glucose, amino acids, salts, trace elements and fatty acids. The proprietary stock culture medium is free of serum, proteins, growth factors and peptones. The proprietary stock culture medium is animal component free. The proprietary stock culture medium contains an inorganic iron source for supplying cells with iron. The proprietary stock culture medium does not contain recombinant albumin and does not contain recombinant transferrin. The proprietary stock culture medium is supplemented with 6 mM L-glutamine prior to use. The proprietary culture medium has an osmolality of 330 mOsmol/kg $H_2O$ and a pH of 7.2.

Clonal cell growth was promoted in the cloning medium independent of the applied stock culture medium, demonstrating that the stock culture media recipe do not play a role for clonal cell growth.

Cloning Medium

Two different cloning medium was applied. First, a commercially available culture medium with unknown recipe (CD CHO, GIVCO®, 10743) and second a proprietary cloning medium with following characteristics: The proprietary cloning medium contains all necessary substances for cell growth, cell viability and cellular productivity, such as but not limited to glucose, amino acids, salts, trace elements and fatty acids. The proprietary cloning medium is free of serum, proteins, growth factors and peptones. The proprietary cloning medium is animal component free. The proprietary cloning medium contains as inorganic iron source Iron (III) phosphate (SIGMA™, F1523) at a concentration of 2 mg/l. The proprietary cloning medium does not contain recombinant albumin and does not contain recombinant transferrin. The proprietary cloning medium is supplemented with 2 mM L-glutamine prior to use. The proprietary cloning medium has an osmolality of 290 mOsmol/kg $H_2O$ and a pH of 6.9.

Clonal cell growth was promoted in both cloning media demonstrating that the stock culture media recipe do not play a role for clonal cell growth. However, important for clonal cell growth were the inventive steps, e.g. supplementation of the cloning media with recombinant proteins as described below.

Single Cell Cloning by Limited Dilution

Limited dilution (LD) was performed by diluting the cell suspension of stock culture from a cell density of higher than $3 \times 10^5$ cells/ml to a cell density of 4 cells/ml (=0.6 cells/150 µl) manually. Cells were diluted in 1:10 steps in cloning medium with a final dilution step of 1:20 in respective supplemented cloning medium. 0.6 cells per well were pipetted in 96-well U-bottom plates (NUNC™) with 150 µl medium per well. The number 0.6 cells/well is the statistical seeding cell density. In reality, when plates were monitored microscopically after seeding, some wells contained no cells and some wells contained 2 or more cells.

Single Cell Cloning by FACS

Single cell cloning (SCC) by FACS (fluorescent activated cell sorting) was performed by sorting 1 cell per well directly into 96-well U-bottom plates (NUNC™). Plates were already provided with 150 µl cloning medium per well. The plates with medium were incubated in incubator prior to cell sorting. FACS sorting was performed in single cell sort mode with a FACSARIA™ (BD™ Biosciences) equipped with an automated cell deposition unit (ACDU).

Incubation and Evaluation

After conducting the SCC, the plates were immediately transferred into the incubator (37° C., 7.5% $CO_2$). The number of successfully expanded clones was evaluated by eye and by microscope 14 days after seeding of single cells. Results are shown as % cloning efficiency. 100% cloning efficiency in each experiment was set to the number of colonies grown in parallel running positive controls supplemented with 10% FBS (GIBCO®, heat inactivated). Since cells were not always in identical growth phases when used for SCC, variations in cloning efficiency occurred between different experiments. This inter-assay variation however, did not distort the overall observations made throughout the study.

Example 1

Comparison of Conditioned Medium and rHSA as Culture Media Additive to Promote Single Cell Growth Goal of the experiment was to evaluate whether conditioned medium or recombinant human serum albumin as additive in culture media can promote cell growth when a cell culture is seeded with extremely low cell concentration, e.g. at single cell status.

CHO Clone23 cells were single cell cloned by limited dilution manually as described in material and methods section. For every medium combination two 96 well plates were plated out. Experiment was performed as follows:

Positive control (FBS): The cloning medium was supplemented with 10% heat inactivated qualified fetal bovine serum (FBS) from GIBCO® (10100-147). This means 40 ml cloning medium was supplemented with 4 ml FBS (100% stock solution).

Conditioned medium K1: Conditioned medium was prepared from CHO-K1 cultures. CHO-K1 cells were cultured in a shake flask in batch. Conditioned medium was separated from CHO-K1 cells by two centrifugation steps. Initially, cell suspension was centrifuged at 190×g for 3 min at room temperature. Supernatant was then transferred into a new vessel and centrifuged again at 3000×g for 10 min at room temperature. Subsequently, the medium was filtered through a 0.2 µm filter (ACRODISC®, PALL). The fresh cloning medium was diluted with 50% so prepared conditioned medium. This means, 20 ml fresh cloning medium was mixed with 20 ml conditioned medium.

Addition of recombinant human serum albumin (rHSA): The cloning medium was supplemented to the final concentration of 2 g/l with recombinant human serum albumin (rHSA) stock solution. This means, 40 ml fresh cloning medium was supplemented with 1.6 ml of a 50 g/l stock solution of rHSA (SIGMA™, A7223).

The plates were incubated as described in material and methods section and the arising colonies were counted.

Results demonstrate (FIG. 1) that conditioned medium is not sufficient to support clonal growth. The rHSA supports the clonal growth, but the cloning efficacy is not sufficient when compared to the control.

Example 2

Test of Recombinant Human Serum Albumin with and Without Addition of Recombinant Human Transferrin Goal of the experiment was to evaluate whether it is possible to increase the cloning efficacy by adding recombinant human transferrin.

CHO Clone23 cells were single cell cloned by limited dilution manually as described in material and methods section. For every media combination two 96 well plates were plated out. Experiment was performed as follows:

Positive control (FBS): The cloning medium was supplemented with 10% heat inactivated qualified fetal bovine serum (FBS) from GIBCO® (10100-147). This means 40 ml cloning medium was supplemented with 4 ml FBS (100% stock solution).

Negative control (without supplement): 40 ml pure cloning medium was used without any further supplementation.

Addition of recombinant human serum albumin (rHSA): The fresh cloning medium was supplemented to the final concentration of 2 g/l with recombinant human serum albumin (rHSA). This means, 40 ml fresh cloning medium was supplemented with 1.6 ml of a 50 g/l stock solution of rHSA (SIGMA™, A7223).

Addition of recombinant human serum albumin and recombinant human transferrin (rHSA+rHTR): The fresh cloning medium was supplemented to the final concentration of 2 g/l with recombinant human serum albumin (rHSA) and further supplemented to the final concentration of 5 mg/l with recombinant human transferrin (rHTR). This means, 40 ml fresh cloning medium was supplemented with 1.6 ml of a 50 g/l stock solution of rHSA and with 10 µl of a 20 g/l stock solution of rHTR MIILLIPORE™ (9701-10).

The plates were incubated as described in material and methods section and the arising colonies were counted.

Results demonstrate (FIG. 2) that without any supplement (negative control) no colonies are visible. When the fresh cloning medium is supplemented with 2 g/l rHSA to the final concentration, around 20% colonies of the control are growing. Surprisingly, when the cloning medium is supplemented with rHSA and rHTR, the number of growing colonies increases up to 80% of the positive control. It is interesting, that the CHO clone 23 cell line used in this experiment was cultured in a culture medium without any proteins during stock culture. The stock culture medium contains an inorganic iron source, and the good growth in stock culture is an evidence of cellular independence from proteins. The data demonstrate, that in single cell status the cells need rHSA and rHTR for better growth even tough they do not need these recombinant proteins in a cell population. These results demonstrate that the high colony growth might be only due to the addition of rHTR. Hence it was interesting to observe, what impact the exclusive addition of rHTR has without involvement of rHSA (see experiment 3).

Example 3

Evaluating the Impact of rHSA and rHTR Separately

Goal of the experiment was to test the recombinant human serum albumin (rHSA) and recombinant human transferrin (rHTR) separately and in combination in order to see the effect of each protein separately. Further goal was to evaluate if a synergistic effect of both proteins does exist.

CHO Clone23 cells were single cell cloned by limited dilution manually as described in material and methods section. For every media combination two 96 well plates were plated out. Experiment was performed as follows:

Positive control (FBS): The cloning medium was supplemented with 10% heat inactivated qualified fetal bovine serum (FBS) from GIBCO® (10100-147). This means 40 ml cloning medium was supplemented with 4 ml FBS (100% stock solution).

Addition of recombinant human serum albumin (rHSA): The fresh cloning medium was supplemented to the final concentration of 2 g/l with rHSA. This means, 40 ml fresh cloning medium was supplemented with 1.6 ml of a 50 g/l stock solution of rHSA (SIGMA™, A7223).

Addition of recombinant human transferrin (rHTR): The fresh cloning medium was supplemented with 5 mg/l to final concentration of recombinant human transferrin (rHTR). This means, 40 ml fresh cloning medium was supplemented with 10 µl of a 20 g/l stock solution of rHTR MILLIPORE™ (9701-10).

Addition of recombinant human serum albumin and recombinant human transferrin (rHSA+rHTR): The fresh cloning medium was supplemented to the final concentration of 2 g/l with recombinant human serum albumin (rHSA) and further supplemented to the final concentration of 5 mg/l with recombinant human transferrin (rHTR). This means, 40 ml fresh cloning medium was supplemented with 1.6 ml of a 50 g/l stock solution of rHSA and with 10 µl of a 20 g/l stock solution of rHTR MIILLIPORE™ (9701-10).

The plates were incubated as described in material and methods section and the arising colonies were counted.

The results demonstrate (FIG. 3) that rHSA and rHTR have either no improvement or only little improvement of cloning efficacy if they are applied separately. Surprisingly, when both proteins are combined in the same medium, the cloning efficacy increases significantly up to 90% of the FBS containing medium.

Example 4

Titration of Recombinant Human Transferrin with and Without Addition of Recombinant Human Serum Albumin Goal of the experiment was if the growth promoting effect of both proteins is concentration dependent.

Clone23 cells were single cell cloned by limited dilution manually as described in material and methods section. For every media combination two 96 well plates were plated out. Experiment was performed as follows:

Positive control (FBS): The cloning medium was supplemented with 10% heat inactivated qualified fetal bovine serum (FBS) from GIBCO® (10100-147). This means 40 ml cloning medium was supplemented with 4 ml FBS (100% stock solution).

Addition of recombinant human transferrin (rHTR): The fresh cloning medium was supplemented with increasing concentrations of recombinant human transferrin (rHTR). Following final concentrations of rHTR have been adjusted by addition of 20 g/l stock solution of rHTR MILLIPORE™ (9701-10) into the fresh cloning medium: 5 mg/1, 50 mg/1, 100 mg/l and 200 mg/l.

Addition of recombinant human transferrin and recombinant human serum albumin (rHTR+rHSA): The fresh cloning medium was supplemented to the final concentration of 2 g/l with recombinant human serum albumin (rHSA). In all this experiments the concentration of rHSA was kept constant. The rHSA supplemented medium was further supplemented with varying amounts of recombinant human transferrin (rHTR). Following final concentrations of rHTR have been adjusted by addition of 20 g/l stock solution of rHTR (MIILLIPORE™, 9701-10) into the fresh cloning medium:

2 g/l rHSA+5 mg/l rHTR 2 g/l rHSA+50 mg/l rHTR 2 g/l rHSA+100 mg/l rHTR 2 g/l rHSA+200 mg/l rHTR

The plates were incubated as described in material and methods section and the arising colonies were counted.

The results clearly demonstrate (FIG. 4) the synergistic effect of both proteins. rHTR alone is not capable to promote cell growth. In previous experiments it has been shown, that only rHSA promotes the cell growth approximately up to 20% of the control. The best cell growth promoting effect is visible by combination of both proteins. Interestingly a very low concentration (5 mg/l) of rHTR is sufficient to achieve cell growth up to 90% of the control cultures.

Example 5

Single Cell Cloning Experiments with Different CHO Cell Lines by FACS Equipped with Automatic Cell Deposition Unit Goal of the experiment was to test the recombinant human serum albumin (rHSA) and recombinant human transferrin (rHTR) in combination with different CHO cell lines. Further goal was to evaluate if this medium formulation successfully expands these cells when they are single cell cloned by FACS and deposited by a robotic unit.

CHO Clone23, CHO K1, and CHO DG44 cells were single cell cloned automatically by FACS as described in material and methods section. For every media combination two 96 well plates were plated. The experiment was performed as follows:

Positive control (FBS): The cloning medium was supplemented with 10% heat inactivated qualified fetal bovine serum (FBS) from GIBCO® (10100-147). This means 40 ml cloning medium was supplemented with 4 ml FBS (100% stock solution).

Addition of recombinant human serum albumin and recombinant human transferrin (rHSA+rHTR): The fresh cloning medium was supplemented to the final concentration of 2 g/l with recombinant human serum albumin (rHSA) and further supplemented to the final concentration of 5 mg/l with recombinant human transferrin (rHTR). This means, 40 ml fresh cloning medium was supplemented with 1.6 ml of a 50 g/l stock solution of rHSA and with 10 µl of a 20 g/l stock solution of rHTR MIILLIPORE™ (9701-10).

The plates were incubated as described in material and methods section and the arising colonies were counted.

The results demonstrate the effect of the combined addition of rHSA and rHTR for promoting cell growth of single cells deposited by FACS (FIG. 5). Additionally, these results show the effectiveness of this medium formulation for different CHO cell lines. Due to the robust growth of CHO K1 cells, the effects of rHSA and rHTR are not as pronounced when compared with CHO clone23 or CHO DG44 cells. Remarkably, when cells were seeded by FACS, they grow in rHSA and rHTR supplemented medium even better than the cells grown seeded manually by limited dilution.

The invention claimed is:

1. A method for the cultivation of a population of cells in a serum free cell culture medium, wherein the cells of the population of cells are cells which are able to grow in an animal component free medium and wherein the population of cells has a cell concentration of less than 100 cells/ml, comprising the steps of:
   a) culturing a population of cells at a cell concentration greater than 100 cells/ml in a first serum free cell culture medium;
   b) reducing the cell concentration to less than 100 cells/ml;
   c) culturing the cells in a second serum free cell culture medium, wherein the second serum free cell culture medium contains recombinant albumin and recombinant transferrin; and
   d) culturing the cells in a third serum free cell culture medium which has a lower concentration of recombinant transferrin and/or recombinant albumin than the cell culture medium of step c).

2. The method according to claim 1, wherein the reducing step in b) comprises isolating a single cell out of the population of cells.

3. The method according to claim 1, wherein the cells of the population of cells do not require recombinant transferrin and/or recombinant albumin for growth, when the cells are cultured at a cell concentration greater than 100 cells/ml.

4. The method according to claim 1, wherein the cells of the population of cells are cells which are adapted to grow in an animal component free medium.

5. The method according to claim 1, wherein the animal component free medium is a protein free medium.

6. The method according to claim 1, wherein the cell culture medium used in step a) contains less recombinant albumin and less recombinant transferrin than the cell culture medium used in step c).

7. The method according to claim 1, wherein the cell culture medium used in step a) and/or in step c) is an animal component free medium.

8. The method according to claim 1, wherein the cell culture medium of step d) is free of recombinant transferrin and recombinant albumin.

9. The method according to claim 1, wherein the cell culture medium of step c) has an osmolality between 280 and 320 mOsmol/kg $H_2O$ and a pH between 6.8 and 7.1.

10. The method according to claim 1, wherein the cell culture media used in steps a) and c) contain L-glutamine in a concentration lower than 4 mM.

11. The method according to claim 1, wherein the cell culture media used in steps a) and c) contain a non-transferrin bound iron.

12. The method according to claim 1, wherein the cells are cultured in step c) for at least 6 days.

13. The method according to claim 1, wherein the cells are cultured in step c) for at least 6 days.

14. The method according to claim 1, wherein in step c) the culture volume is at most 1 ml.

15. The method according to claim 1, wherein the cell culture medium used in step c) contains at least 100 mg/l recombinant albumin and at least 0.5 mg/l recombinant transferrin, preferably at least 2000 mg/l recombinant albumin and at least 5 mg/l recombinant transferrin.

16. The method according to claim 2, wherein the single cell is isolated by an automatic cell sorting system.

17. The method according to claim 1, wherein the population of cells is a CHO cell line.

* * * * *